United States Patent [19]

Schulte

[11] Patent Number: 4,486,178
[45] Date of Patent: Dec. 4, 1984

[54] TOOTH IMPLANT MADE OF METAL

[75] Inventor: Willi Schulte, Tüingen, Fed. Rep. of Germany

[73] Assignee: Friedrichsfeld GmbH Steinzeug-und Kunststoffwerke, Mannheim, Fed. Rep. of Germany

[21] Appl. No.: 521,663

[22] Filed: Aug. 10, 1983

[30] Foreign Application Priority Data

Aug. 14, 1982 [DE] Fed. Rep. of Germany ....... 3230374

[51] Int. Cl.³ .............................................. A61C 8/00
[52] U.S. Cl. ................................... 433/173; 433/174; 433/176
[58] Field of Search ................ 433/173, 174, 175, 176

[56] References Cited

U.S. PATENT DOCUMENTS

| | | | |
|---|---|---|---|
| 3,827,145 | 8/1974 | Richards | 433/175 |
| 4,016,651 | 4/1977 | Kawahara et al. | 433/174 |
| 4,050,157 | 9/1977 | Fagan, Jr. et al. | 433/176 |
| 4,318,696 | 3/1982 | Kasama et al. | 433/173 |

FOREIGN PATENT DOCUMENTS

| | | | |
|---|---|---|---|
| 2413883 | 9/1975 | Fed. Rep. of Germany | 433/174 |
| 2619650 | 11/1977 | Fed. Rep. of Germany | 433/174 |

*Primary Examiner*—John J. Wilson
*Attorney, Agent, or Firm*—Fisher, Christen & Sabol

[57] ABSTRACT

The invention provides a implants made of metal for the purpose of anchoring superstructures consisting of one or more crowns or parts of crowns, also made of metal, arranged in the form of bridges. In general, various metals are used for the implant and the individual parts of the superstructure. In most of the implant systems presently in use, these different metal parts are in direct, electrically conductive contact. Consequently, the possibility of the formation of galvanic cells results. The electrical voltages coming into being as a result of such can lead to the flowing of electric currents through the tissue and the body fluid that is present. Such electrical currents, in turn, can have an unfavorable influence on the tissue reactions at the point where the surface is in contact with the implant, and consequently can result in the premature loosening and loss of the implant. By galvanically separating the superstructure and the implant by inserting aluminum oxide ceramic parts such problem is eliminated. Furthermore, it is suggested that such aluminum oxide ceramic parts be placed on the side of the implant projecting into the mouth in such a way that mucous membrane is embedded in a bacteria-proof manner in a groove provided on the outside of the implant.

3 Claims, 3 Drawing Figures

TOOTH IMPLANT MADE OF METAL

BACKGROUND OF THE INVENTION

1. Field of the Invention

The invention relates to teeth implants made of metal.

2. Prior Art

There are implants made of metal to anchor superstructures made up of one or more crowns or parts of crowns, also containing metal, in the form of bridges. The implant consists of an actual implant body which is embedded in the jaw and a part bearing the superstructure which sets up the connection between the actual implant body and the superstructure and is surrounded by the mucous membrane. Implants of such type have been known for quite a long while and are available in various forms. The forms of the actual implant body can be screws or forms which are derived from screws. They also can be shaped like leaves or, as has recently been suggested, they can have the form of hollow cylinders. Such implants consist of another part, in addition to the actual implant body, which provides connection with the oral cavity through the mucous membrane. Such part can either be connected with the implant body to form a single piece or it can be screwed onto the actual implant body, sometimes only later and in a second operation, or can be fastened to it in some other way. The superstructure is placed on this part of the implant that projects into the oral cavity. This superstructure can either consist of a single crown or of a bridge, which then usually holds several crowns. If that is the case, the implant serves as a bridge support.

In most metal implants up to the present, an electrically conductive connection exists between the actual implant body and the part bearing the superstructure and the crown. If different metals occur at any place in this overall construction, an electrical element is formed in working together with the saliva which functions as an electrolyte and the adjoining tissue parts which also function as electrolytes. Since, in general, and with most of the known implants, only one metal is used in the implant itself and its component parts, the metal used in the crown will be the chief cause of the formation of this galvanic cell in this general case. The occurrence of such galvanic cells in the mouth area is particularly harmful when a part of the flow of current caused by this cell passes through the tissue of the mucous membrane and the adjoining bone. Specifically, a polarization of the cell membranes occurs then which can bring about pathological changes. Furthermore, a transfer of material can occur which brings about a shift in the equilibrium of the concentrations so that optimum physiological conditions no longer prevail in all areas of the tissue adjoining the surface of the implant. This, in turn, can bring about degeneration of the tissue in the immediate neighborhood of the implant from which a contribution to premature loss of the implant may occur. Naturally, this effect is especially likely to have drastic consequences when several implants are connected by bridge structures, since electric currents will then flow through large areas of the jaw in a completely unphysiological manner.

A solution to this complex problem is available through the use of ceramic implants, that is, non-conductive implants. However, there are cases in which metal implants have to be used for reasons of size and mechanical stability. This is made possible by the fact, among other things, that there are metals which have similar qualities of compatibility whith various substances, as is the case, for example, with extremely pure aluminum oxide, ceramics that are resistant to breaking. The most important metal that satisfies this requirement is titanium. Some alloys with a high titanium content are also suitable.

BROAD DESCRIPTION OF THE INVENTION

An object of the invention is to prevent the formation of galvanic cells when metal implants for teeth are used, even when other metals are used in the area of the superstructure than are used in the actual implant. Other objects and advantages of the invention are set out herein or are obvious herefrom to one ordinarily skilled in the art.

The objects and advantages of the invention are achieved by the tooth implant of the invention.

To accomplish the invention objects, the invention provides for placing a ceramic part between the implant and the superstructure which electrically insulates them from each other.

More specifically, the invention involves teeth implant made of metal for anchoring superstructures having one or more crowns or parts of crowns, also made of metal, arranged in the form of bridges. The implant is an actual implant body which is inserted in the jaw and a part bearing the superstructure. The superstructure bearing part provides the connection between the actual implant body and the superstructure and provides the passage of the implant through the mucous membrane (of the gum). A ceramic part is located between the implant and the superstructure that separates them electrically from each other.

Locating the insulating ceramic part within the passage through the mucous membrane of the gum is particularly preferred and effective. Another variant is the providing of the insulating part in the area of the passage through the mucous membrane with a groove traversing it circumventionally.

The implant of the invention has the advantage that the formation of the galvanic element used between the metals of the crown and the metal of the actual implant body cannot be formed in such a way that a metallic, electrically conductive connection, and consequently an electric short circuit exists between the two metals. By this means, any irritation of the tissue which might originate with this galvanic cell is avoided to the greatest possible extent. Since this irritation of the tissue could lead to the loosening of the implant, one of the two contributing factors which might lead to loosening of the implant is also thereby avoided, or at least reduced to an insignificant matter by this means.

BRIEF DESCRIPTION OF THE DRAWINGS

The invention is explained in greater detail by the various embodiments with the help of the drawings, but such description does not constitute a limitation. In the drawings.

DETAILED DESCRIPTION OF THE INVENTION

Figure 1:
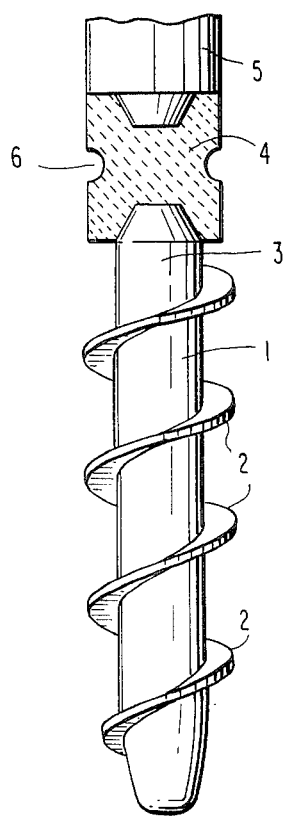
FIG. 1 is a partially-cutaway front elevational view of an implant of the invention which has an implant body that is essentially screwlike in shape.

The actual tooth implant body is designated by numeral 1 in FIG. 1. Implant body 1 has spiral passages 2 which are shown as having broad surfaces. The part of the implant that bears the superstructure (not shown) is designated with the numeral 3. Numeral 4 refers to the electrically insulating ceramic part introduced by the invention. Part 5, which anchors the superstructure (not shown), can be seen above ceramic part 4. In the case of FIG. 1, insulating ceramic part 4 has two drilled holes located axially one behind the other, which serve the purpose of receiving pins that are located at the upper end of implant body 1 and at the lower end of part 5 that anchors the superstructure. The groove, which serves the purpose of helping to fit the device to the mucous membrane in this area, is designated by numeral 6.

Figure 2:
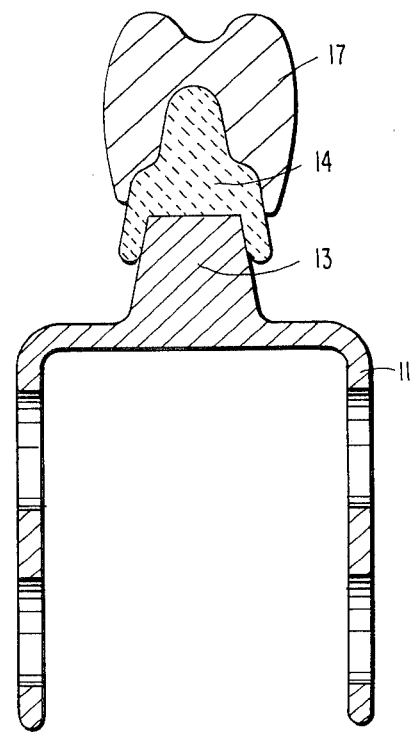
FIG. 2 is a partially-cutaway front elevational view of an implant of the invention which consists essentially of a cylinder that is open on one side.

In FIG. 2, numeral 11 refers to the actual implant body, which has part 13 bearing the superstructure at its upper end. Above that, in turn, is located insulating ceramic part 14 of the invention, above which single crown 17 is shown in this instance. In this case, part 13 of the implant bearing the superstructure, in turn, projects into insulating ceramic part 14, while superstructure 17 surrounds a pinlike attachment of part 14 which is directed upwards.

Figure 3:
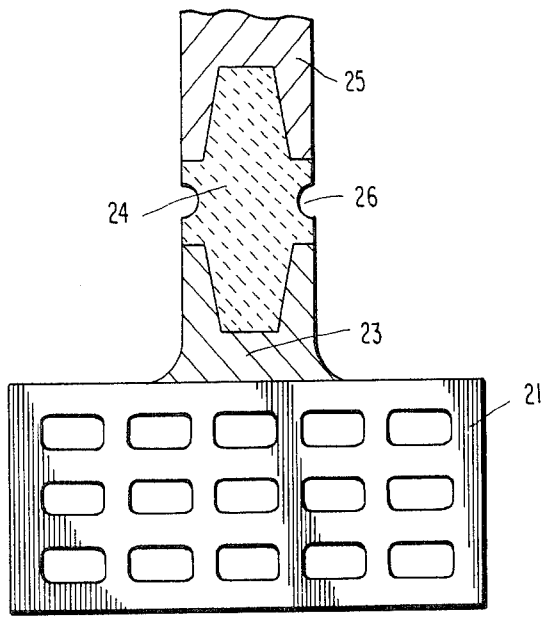
FIG. 3 is a partially-cutaway front elevational view of one of several possible and usual embodiments of the leaf-shaped implants of the invention.

In FIG. 3, actual implant body 21 has a leaflike shape. In this case, the leaflike implant also has openings. Part 23 which sets up the connection with the superstructure has a bagshaped receptacle into which insulating ceramic part 24 of the invention projects as a pin. Part 24 also has a pin on its other side which is surrounded by part 25 which serves to anchor the superstructure. Insulating ceramic part 24, in turn, has groove 26 that traverses its circumference and serves the purpose of fitting the device to the mucous membrane.

Such grooves in the area of the passage through the mucous membrane have already proved their value in other implant structures. The way the metal implants are made in accordance with the invention makes it possible to make use of this reliable arrangement in the area of the passage through the mucous membrane for metal implants too, and consequently to accomplish the invention's purpose of electrically separating the superstructure and the implant body.

By way of summary, the invention involves an implant for anchoring a dental prosthesis which includes a metal implant body for inserting in the jaw bone, a metal superstructure comprising the dental prosthesis or part thereof, and an insulating ceramic part located between and connecting the implant body to the superstructure. The ceramic part electrically isolates the implant body from the superstructure. The insulating ceramic part can be located on the implant such that when the implant is inserted in the jaw bone, the ceramic part will be at the level of the mucous membrane. The insulating ceramic part can have an annular groove for fitting the part to the mucous membrane.

What is claimed is:

1. An implant for anchoring a dental prosthesis comprising a metal implant body for inserting in the jaw bone, a metal superstructure comprising said dental prosthesis or part thereof, and an insulating ceramic part located between and connecting said implant body to said superstructure, said ceramic part electrically isolating said implant body from said superstructure.

2. An implant as claimed in claim 1 wherein said insulating ceramic part is located on the implant such that when said implant is inserted in the jaw bone, said ceramic part will be at the level of the mucous membrane.

3. An implant as claimed in claim 2 wherein said insulating ceramic part has an annular groove for fitting said ceramic part to the mucous membrane.

* * * * *